United States Patent [19]

Kinoshita

[11] 4,281,646

[45] Aug. 4, 1981

[54] CLEANING DEVICE FOR AN OBSERVATION WINDOW OF AN ENDOSCOPE

[75] Inventor: Kunio Kinoshita, Hachioji, Japan

[73] Assignee: Olympus Optical Co., Ltd., Tokyo, Japan

[21] Appl. No.: 51,244

[22] Filed: Jun. 22, 1979

[30] Foreign Application Priority Data

Jun. 30, 1978 [JP] Japan .................................. 53/79460
Dec. 18, 1978 [JP] Japan ................................ 53/156204

[51] Int. Cl.³ ............................................... A61B 1/06
[52] U.S. Cl. ..................................... 128/6; 15/250.02; 350/63; 134/104; 134/113
[58] Field of Search ......................... 128/3-8; 350/61, 63; 15/250.02, 250.01, 250 A; 134/104, 113

[56] References Cited

U.S. PATENT DOCUMENTS

| | | | |
|---|---|---|---|
| 2,243,285 | 5/1941 | Pope | 128/6 |
| 3,117,727 | 1/1964 | Pollock et al. | 15/250 A |
| 3,903,877 | 9/1975 | Teraba | 350/63 |
| 4,204,528 | 5/1980 | Termanini | 128/6 |

FOREIGN PATENT DOCUMENTS

32377 12/1970 Japan .......................................... 128/6

*Primary Examiner*—Robert W. Michell
*Assistant Examiner*—Arthur S. Rose

[57] ABSTRACT

A cleaning device comprises a fluid passage extending through the sheath of a forward view type endoscope and having one end located in the operation section of the endoscope and the other end located in the distal end section of the endoscope; a pump for supplying a fluid through the fluid passage from the operation section; a nozzle disposed in the distal end portion and communicating at its proximal end with said other end of the fluid passage; a reciprocating device for projecting the distal end portion of the nozzle from the distal end of the distal end section and retracting the nozzle into the distal end section; and a nozzle opening which is directed to an observation window provided on the distal end when the nozzle is projected from the distal end and which is closed by the distal end section when the nozzle is retracted in the distal end section.

16 Claims, 14 Drawing Figures

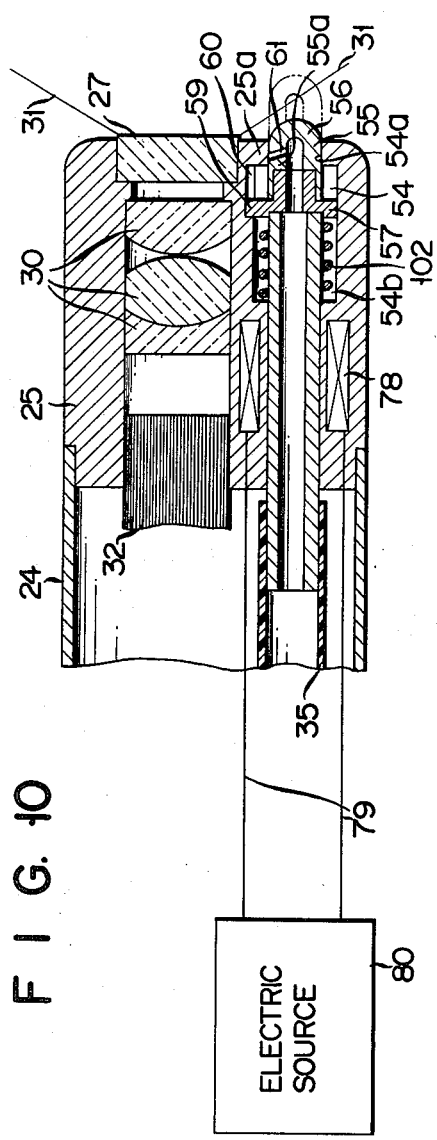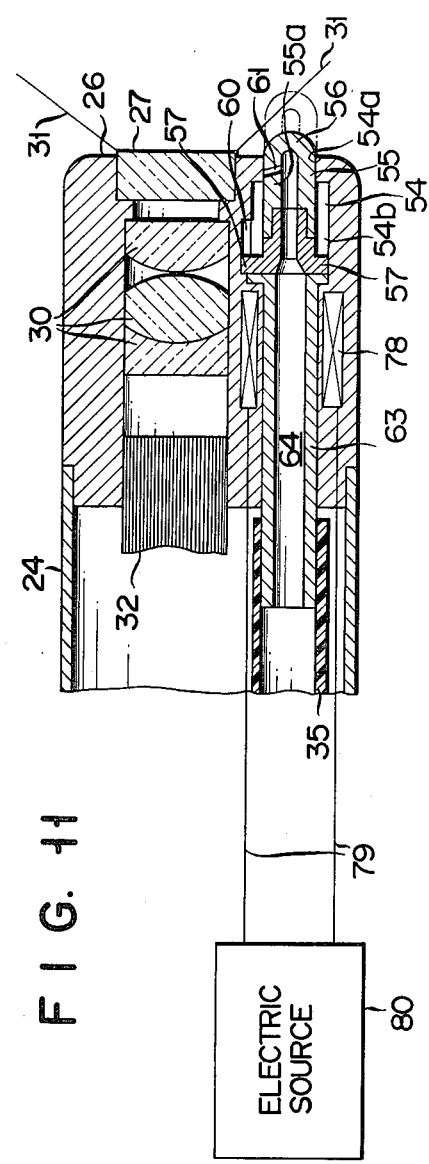

CLEANING DEVICE FOR AN OBSERVATION WINDOW OF AN ENDOSCOPE

BACKGROUND OF THE INVENTION

This invention relates to a cleaning device which is provided with an improved nozzle for applying a cleaning fluid onto the outer surface of an observation window provided on the distal end of a forward view type endoscope.

While an elongated sheath of an endoscope is inserted in a body cavity, the blood and other body fluids (hereinafter called "dirt") stick onto the outer surface of an observation window provided on the distal end of the endoscope, often making it impossible to observe the interior of the body cavity. To avoid this trouble, it has been practiced that a nozzle is provided to apply a cleaning fluid onto the outer surface of the observation window, thus washing down the dirt.

In order to wash down the dirt easily, the nozzle must be projected from the distal end of the endoscope. When an endoscope whose sheath is as thin as 7 to 8 mm or so and whose angle of view is very large such as 90 to 100° is used, the nozzle inevitably comes into the field of view of the endoscope to disturb the observation of a body cavity interior.

SUMMARY OF THE INVENTION

It is an object of this invention to provide a cleaning device for an observation window of an endoscope, provided with a nozzle which projects from the distal end of the endoscope when a cleaning fluid is applied onto the outer surface of the observation window and which recedes into the distal end section of the endoscope at least when the interior of an body cavity is observed, thereby enabling the interior of the body cavity to be fully observed.

A cleaning device according to this invention comprises a fluid passage extending through the sheath of a forward view type endoscope and having one end located in the operation section of the endoscope and the other end located in the distal end section of the endoscope; means for supplying a fluid through the fluid passage from the operation section; a nozzle disposed in the distal end portion and communicating at its proximal end with said other end of the fluid passage; reciprocating means for projecting the distal end portion of the nozzle from the distal end of the distal end section and retracting the nozzle into the distal end section; and a nozzle opening which is directed to an observation window provided on the distal end when the nozzle is projected from the distal end and which is closed by the distal end section when the nozzle is retracted in the distal end section.

Between the distal end section and the distal end portion of the nozzle, an O-ring is provided to make it possible to prevent the fluid from flowing from a body cavity into the nozzle through the nozzle when the nozzle is retracted.

BRIEF DESCRIPTION OF THE DRAWING

This invention can be fully understood from the following detailed description with reference to the accompanying drawings in which:

FIGS. 10 and 11 are vertical cross sectional views of other movable nozzles according to this invention.

DESCRIPTION OF THE PREFERRED EMBODIMENTS

Figure 1:
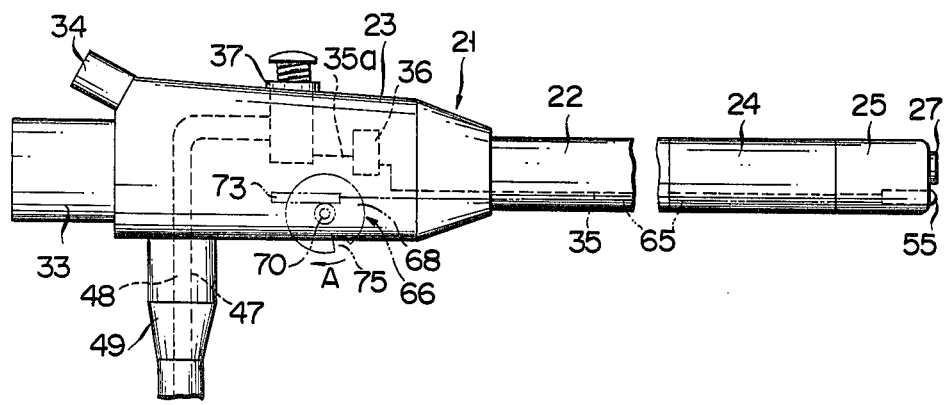
FIG. 1 is a side view of a forward view type endoscope provided with a cleaning device according to this invention.

As shown in FIG. 1, an endoscope 21, to which a cleaning device according to this invention is applied, is a forward view type which comprises an elongated sheath 22, an operation section 23 secured to the proximal end of the sheath 22, and a distal end section 25 secured to the distal end of a flexible tube 24 forming a distal end portion of the sheath 22. When inserted into a body cavity, the sheath 22 can bend according to the configuration of the body cavity. The flexible tube 24 is arbitrarily bent by push or pull, at the operation section 23, of operating wires (not shown) extending through the elongated sheath 22. This mechanism for bending the flexible tube 24 is known and is not the object of this invention, its description being omitted.

Figure 3:
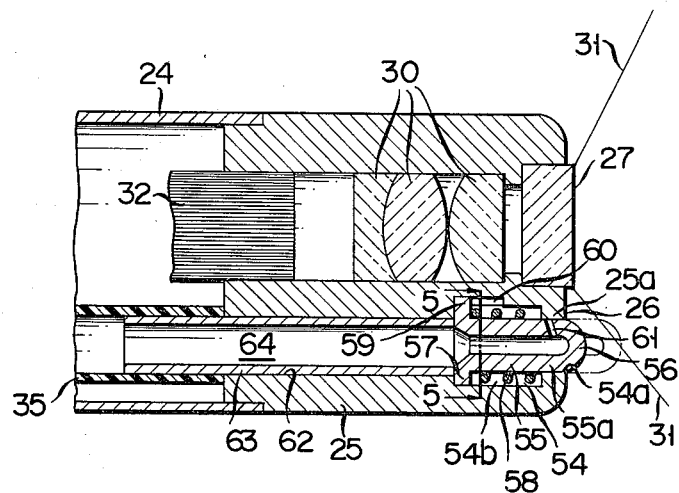
FIG. 3 is a cross sectional view of the distal end section of the endoscope provided with a movable nozzle and a bias means for retracting the nozzle into the distal end section, taken along line 3—3 in FIG. 4.
Figure 4:
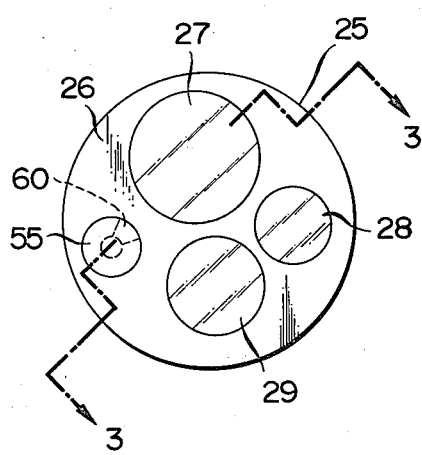
FIG. 4 is a front view of the distal end of the endoscope shown in FIG. 1.

As illustrated in FIGS. 3 and 4, the end surface 26 of the distal end section 25 is provided with an observation window 27 and an illumination window 28. Both windows 27 and 28 are made of a transparent glass plate. A channel 29 extends through the sheath 22 to guide a forceps, a catheter or a fluid and opens at the end surface 26.

In the distal end section 25, as shown also in FIG. 3, a compound lens 30 is aligned with the observation window 27 to provide a wide field of view 31 having an angle of view of, for example, 90° to 100°. (In FIG. 3, the angle of view is exaggerated). A bundle of image guide optical fibers 32 extends through the sheath 22 with its distal end and proximal end optically connected to the compound lens 30 and an ocular section 33 disposed at the proximal end of the operation section 23 (FIG. 1), respectively. Through the ocular section 33 it is possible to observe the interior of a body cavity into which the sheath 22 is inserted. As in the known endoscope, a bundle of illumination optical fibers (not shown) extends also through the sheath 22. Its distal end is positioned to face the illumination window 28, and its proximal end is connected through the operation section 23 to a light source (not shown) which is provided outside the endoscope 21. The light is guided from the light source through the bundle of illumination optical fibers and illumination window 28 in the body cavity so as to illuminate a desired part of the body cavity. As shown in FIG. 1, the proximal end of the operation section 23 has an inlet 34 through which a medical instrument such as a forceps is inserted into the channel 29.

Through the sheath 22 there extends a fluid conducting tube 35 which is made of polyethylene and which constitutes a fluid passage. The distal end of the tube 35 is positioned adjacent to the inner end of the distal end section 25, and its proximal end is connected to a check valve 36 disposed in the operation section 23. Disposed also in the operation section 23 is a fluid selecting valve 37 which communicates with the check valve 36 via a connecting tube 35a (FIG. 1).

Figure 2:
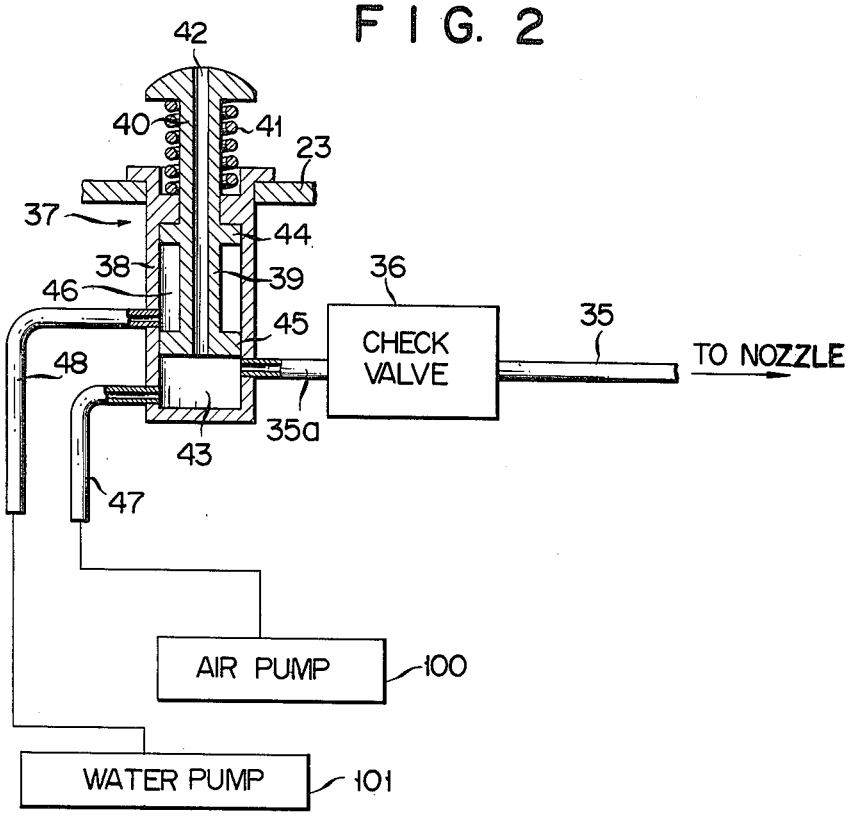
FIG. 2 illustrates a pipe arrangement for supplying fluids selectively to a nozzle in the distal end section of the endoscope shown in FIG. 1.

As shown in FIG. 2, the fluid selecting valve 37 comprises a hollow cylindrical, blind-ended valve housing 38 secured at one end to a lateral wall of the operation section 23, a spool 39 slidably inserted into the housing 38, and a rod 40 which is biased by a coil spring 41 and projected from the operation section 23. The rod 40 is formed integral with the spool 39. The spool 39 and the rod 40 have a through hole 42. As long as the spool 39 is not pushed into the housing 38, an air chamber 43 exists between the free (or lower) end of the spool 39 and the bottom (or blind end) of the housing 39. The spool 39 has lands 44 and 45 at its respective ends, and these lands 44 and 45 define an annular groove 46 therebetween. Thus, the fluid selecting valve 37 is a kind of spool valve.

An air pump 100 and a water pump 101 are provided outside the endoscope 21. An air pipe 47 and a water pipe 48 are connected at their corresponding ends to the pumps 100 and 101, respectively. The pipes 47 and 48 extend through a protection tube 49 projecting from a lateral wall of the operation section 23 and are connected at their other end to the fluid selecting valve 39 in the operation section 23. The air pipe 47 is connected at its other end to the valve 37 in such a way as to communicate with the air chamber 43 and communicate with the connecting tube 35a which opens to the chamber 43 in a position adjacent to the land 45 of the spool 39, when the spool 39 is not moved downward. The water pipe 48 is connected at its other end to the valve 37 in such a way as to communicate always with the annular groove 46 of the spool 39.

As long as the spool 39 is not pushed in the housing 38, the air pipe 47 communicates with the connecting tube 35a through the air chamber 43. But the compressed air from the air pump 100 flows through the hole 42 into the atmosphere if the hole 42 is not plugged. In this case, the compressed air flows into neither the check valve 36 nor the fluid conducting tube 35. When the hole 42 is plugged with, for example, a finger cushion, the compressed air is supplied to the fluid conducting tube 35 through the check valve 36.

When the spool 38 is moved fully downward the connecting tube 35a communicates with the annular groove 46, whereby washing water from the water pump 101 is supplied to the fluid conducting tube 35 through the check valve 36. Thus, the fluid selecting valve 37 works in three different ways, to supply one of the two fluids to the tube 35, to supply the other fluid to the tube 35, and to supply no fluid to the tube 35.

Figure 6:
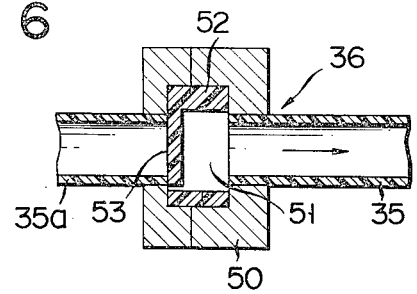
FIG. 6 is a vertical cross sectional view of a check valve disposed in a fluid passage which communicates with the nozzle shown in FIG. 3.

As illustrated in FIG. 6, the check valve 36 comprises a valve housing 50 provided in the operation section 23, a cylindrical valve chamber 51 formed in the valve housing 50 and a hollow cylindrical valve member 52 fitted in the cylindrical valve chamber 51. The valve member 52 is made of polytetrafluoroethylene and has a flap 53 which is formed by circularly cutting the blind end wall of the valve member 52 facing the connecting tube 35a with one portion left uncut. The flap 53 has a diameter larger than the inner diameter of the connecting tube 35a and can thus entirely cover the corresponding end of the connecting tube 35a. The cylindrical valve chamber 51 communicates with the proximal end of the fluid conducting tube 35. The pressurized fluid through the connecting tube 35a such as compressed air or pressurized water flowing pushes the flap 53 to open and then flows into the fluid conducting tube 35. If the pressure in the fluid conducting tube 35 happens to become higher than that in the connecting tube 35a, the flap 53 will close the end of the connecting tube 35a thereby to prevent the fluid flow from the fluid conducting tube 35 into the connecting tube 35a.

Figure 5:
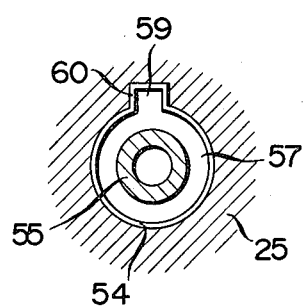
FIG. 5 is a cross sectional view of the nozzle and the nozzle chamber, taken along line 5—5 in FIG. 3.

As shown in FIGS. 3 and 5, a substantially hollow cylindrical nozzle chamber 54 is provided parallel to the compound lens 30 in the distal end section 25. Reciprocatingly inserted into the chamber 54 is a stainless steel hollow cylindrical nozzle 55 blinded at one end 56 such that the distal end portion 55a of the nozzle 55 can project from, and recede into, the end surface 26 of the distal end section 25. The nozzle chamber 54 consists of two parts, one part being a forward cylindrical bore portion 54a defined by the inner cylindrical surface of an inwardly extending annular flange 25a formed in the forward portion of the distal end section 25 and the other part being a remaining increased inner diameter portion 54b. Slidably inserted into the forward bore portion 54a is the distal end portion 55a of the nozzle 55. The nozzle 55 is provided at its proximal end with an outwardly extending annular flange 57 with its outer periphery slidably contacting the inner surface of the remaining portion 54b. In the remaining portion 54b of the nozzle chamber 54, a coil spring 58 surrounds the nozzle 55. The ends of the spring 58 always abut against the flange 25a and the flange 57, respectively. Thus, the coil spring 58 always urges the nozzle 55 toward the operation section 23 so as to retract the nozzle 55 into the chamber 54. A key 59 integrally formed on the outer periphery of the flange 57 slidably engages a key groove 60 formed in the inner wall of the remaining portion 54b of the nozzle chamber 54 along the nozzle 55 so as to prevent the nozzle 55 from rotating. In the lateral wall 55a of the forward portion of the nozzle 55 is formed a nozzle opening 61 which extends so as to be directed to the outer surface of the observation window 27 when the nozzle 55 is projected as indicated by a chain line in FIG. 3.

In the distal end section 25, an elongated bore 62 is provided to extend axially of the distal end section 25. In the bore 62 a connecting tube 63 made of stainless steel is fixedly inserted. One end of the connecting tube 63 communicates with the proximal end of the nozzle 55, and the other end of the tube 63 is tightly inserted into the distal end portion of the fluid conducting tube 35.

When a pressurized fluid 64, that is, compressed air or pressurized washing water is introduced into the fluid conducting tube 35 through the fluid selecting valve 37, it presses the inner surface of the blind end 56 of the nozzle 55 to push the nozzle 55 out into a position indicated by a chain line in FIG. 3. When the nozzle 55 is disposed in said position, the fluid 64 is applied through the nozzle opening 61 onto the outer surface of the observation window 27. If the fluid 64 is washing water, it washes the outer surface of the observation window 27. If it is air, it dries the outer surface of the observation window 27. Thus, to clean the outer surface of the window 27, washing water is used first, and then air is applied. When the fluid selecting valve 37 is brought into such a state as shown in FIG. 2, the supply of the fluid 64 is stopped. The nozzle 55 is then retracted into the nozzle chamber 54, whereby its blind end 56 moves away from field of view 31. In this way, the nozzle 55 does not disturb the observation of the interior of a body cavity.

Now referring to FIG. 7, another embodiment of this invention will be described. This embodiment differs from the embodiment of FIG. 3 in that it uses no connection tube 63. A nozzle 55 extends through a nozzle chamber 54 and an elongated bore 62 in the distal end section 25 of an endoscope, and its proximal end portion is slidably inserted into the distal end portion of a fluid conducting tube 35 in a fluid-tight fashion. The nozzle 55 has a flange 57 which makes slidable contact with the inner surface of the nozzle chamber 54. Between the flange 57 and the proximal end of the chamber 54, a coil spring 102 is provided to always urge the nozzle 55 so that the blind end 56 of the nozzle 55 projects from the distal end section 25 of the endoscope. A steel operating wire 65 extends in the sheath 22 of the endoscope in parallel to the fluid conducting tube 35. One end of the wire 65 is connected to a key 59 formed on the outer periphery of the flange 57. The other end of the wire 65 is pulled by a wire operating mechanism 66 disposed in the operation section 23 of the endoscope. The wire 65 is inserted into a protective spiral tube 67, only a part of which is shown in FIG. 7.

Figure 9:
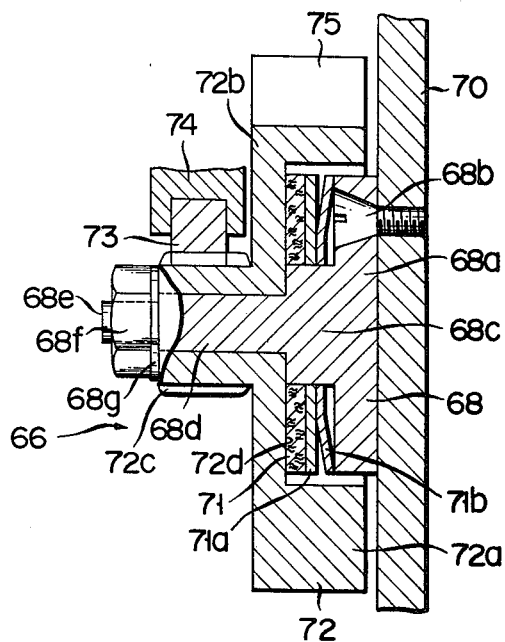
FIG. 9 is a schematical front view of an operating mechanism for a wire used in the embodiments shown in FIG. 7 and FIG. 8.

Referring to FIG. 9, the wire operating mechanism 66 is constructed as follows. A mount 68 has a disc-shaped base portion 68a connected by a screw 68b to a frame 70 provided in the operation section 23, a neck portion 68c having a square cross section and passing central square holes of a friction disc 71 made of cork, a metallic ring 71a and plate spring 71b, a central shaft portion 68d, a male screw 68e projecting therefrom, and a nut 68f engaging therewith. Between the nut 68f and the top end of the shaft 68d, there is interposed a washer 68g. A ring-shaped rotary member 72 comprises a ring portion or a skirt 72a surrounding the disc 71, ring 71a and plate spring 71b, a circular end wall 72b, and a pinion 72c rotatably mounted on the central shaft portion 68d. By tightening the nut 68f, the inner surface 72c makes frictional engagement with the facing surface of the friction disc 71 by the biasing force of the spring 71b. A rack 73 engages the pinion 72c and is slidable lengthwise of the endoscope on another frame 74 in the operation section 23. Said other end of the wire 65 is fixed to the rack 73. The rotary member 72 is provided in its outer periphery with a notch 75 (FIGS. 1 and 9).

Figure 7:
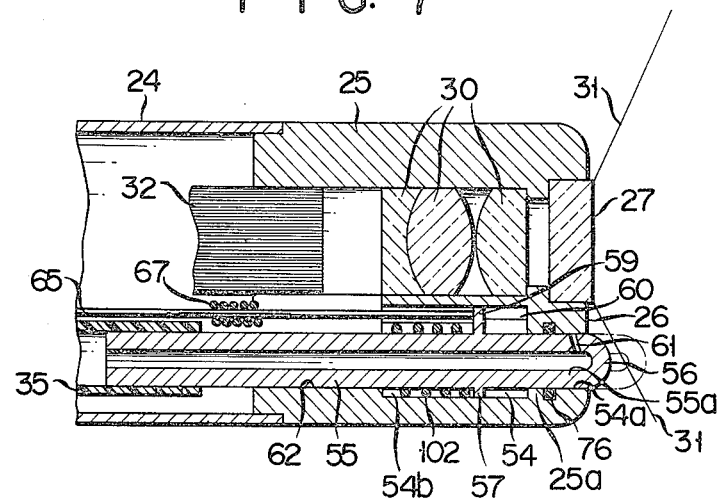
FIGS. 7 and 8 are vertical cross sectional views of other movable nozzles according to this invention.

When the notch 75 of the rotary member 72 is located in such a position as shown in FIG. 1, the rack 73 is in its rearmost position, thus pulling the wire 65 toward the proximal end of the endoscope and keeping the nozzle 55 within the nozzle chamber 54 (see FIG. 7). The friction between the disc 71 and the inner surface 72d of the rotary member 72 surpasses the biasing force of the spring 102. The nozzle 55 therefore does not project from the end surface 26 of the distal end section 25. The nozzle 55 does not project into the field of view 31. To clean an observation window 27, the rotary member 68 is rotated in the direction of arrow A in FIG. 1 until the notch 75 reaches the portion of the lateral wall of the operation section 23 which is the nearest to the proximal end of the endoscope. Then, the rack 73 moves forward, whereby the nozzle 55 is projected by the spring 102 from the end surface 26 of the distal end section 25. Then, the fluid selecting valve 37 is operated to clean the outer surface of the observation window 27. In the flange 57 of the distal end section 25, an O-ring 76 is provided to surround that part of the distal end portion 55a of the nozzle 55 which is a little rearward of a nozzle opening 61, thus providing a fluid-tight seal between the nozzle chamber 54 and the atmosphere.

Figure 8:
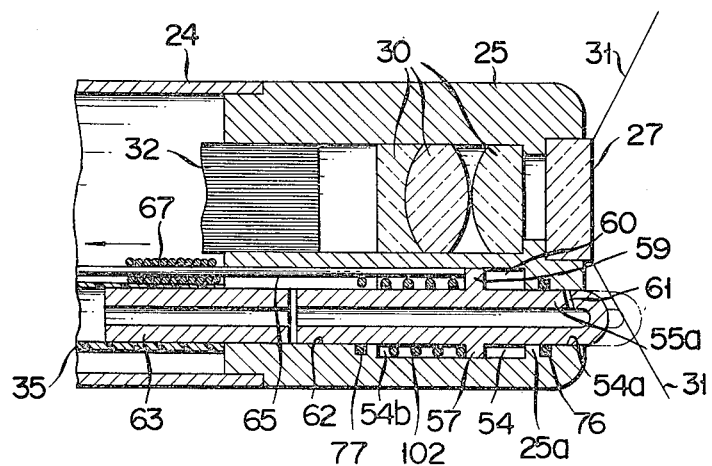

Now referring to FIG. 8, another embodiment of this invention will be described. This embodiment differs from the embodiment of FIG. 7 only in that it uses a connecting tube similar to the tube 63 used in the embodiment of FIG. 3 and an O-ring 77 disposed between the distal end section 25 of an endoscope and the proximal end portion of a nozzle 55. The connecting tube 63 has its proximal end portion tightly inserted in the distal end portion of a fluid conducting tube 35. Since the proximal end portion of the tube 63 does not slide in the tube 35 unlike the nozzle 55 of the embodiment of FIG. 7 which slides in the tube 35, a fluid tightness between the tubes 35 and 63 is ensured.

FIG. 10 shows another embodiment of this invention, in which an electromagnet 78 is used instead of the wire 65 employed in the embodiment of FIG. 7. The electromagnet 78 is disposed in the distal end section 25 of an endoscope 21 in a position a little rearward of a nozzle chamber 54 and surrounds a nozzle 55. The lead wires 79 of the electromagnet 78 extend through the sheath 22 of the operation section 23 of the endoscope 21 and are connected to an electric source 80 provided outside the endoscope 21. The nozzle 55 has a flange 57 which is made of iron and easily attracted to the electromagnet 78. To clean an observation window 27, the power supply from the electric source 80 to the electromagnet 78 is stopped. Now that the flange 57 is not attracted to the electromagnet 78, it is pushed forward by a coil spring 102 disposed in the nozzle chamber 54. As a result, the nozzle 55 projects from the distal end section 25 into a position indicated by a chain line. Then, a fluid selecting valve 37 is operated to clean the outer surface the observation window 27. During the observation of the inferior of a body cavity, power is supplied from the electric source 80 to the electromagnet 78. In this case, the electromagnet 78 pulls the nozzle 55 into the nozzle chamber 54 and thus the nozzle 55 is moved out of a field of view 31. The blind end 56 of the nozzle 55 would therefore not disturb the observation of the interior of a body cavity.

FIG. 11 shows still another embodiment of this invention. This embodiment differs from the embodiment of FIG. 3 only in that a hollow cylindrical electromagnet 78 is disposed in the distal end section 25 of an endoscope 21 and in a position rearward of a nozzle chamber 54 so as to surround a connection tube 63. The lead wires 79 of the electromagnet 78 are connected to an electric source 80 in the same manner as in the embodiment of FIG. 10. As in the embodiment of FIG. 10, the nozzle 55 has a flange 57 which is made of iron. To clean the outer surface of an observation window 27, the pressure of a fluid 64 pushes the nozzle 55 into a position indicated by a chain line after the electric power supply from the electric source 80 has been stopped.

Figure 12:
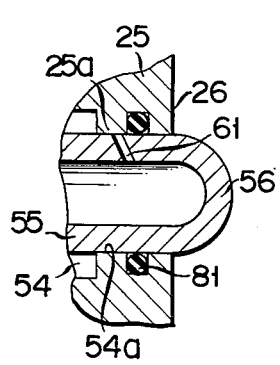
FIGS. 12 to 14 are vertical cross sectional views each showing part of the distal end portion of an endoscope, a nozzle and a ring or rings mounted on the nozzle.
Figure 13:
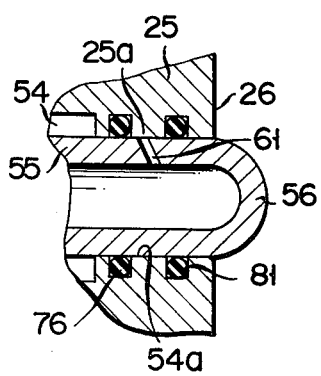
Figure 14:
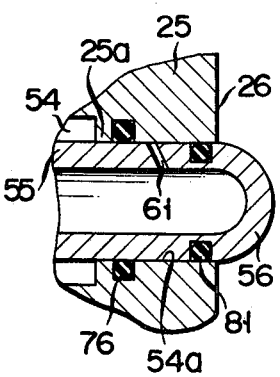

FIGS. 12 to 14 illustrate means for preventing dirt from entering a fluid conducting tube 35 from a body cavity via a nozzle opening 61 and a nozzle 55 when the nozzle 55 recedes into the distal end section 25 of an endoscope 21.

As shown in FIG. 12, said means comprises an O-ring 81 made of silicon rubber or the like and inserted into an annular groove formed in an annular flange 25a formed in the distal end section 25. The inner periphery of the O-ring 81 makes resilient contact with that portion of the distal end portion of the nozzle 55 which is forward of the nozzle opening 61 so long as the nozzle 55 is retracted fully within a nozzle chamber 54 provided in the distal end section 25. The O-ring 81 provides a fluid-tight seal between the flange 25a and the outer periphery of the nozzle 55. Thus, even if the pressure in the fluid conducting tube 35 happens to be lower than that in the body cavity, dirt cannot flow into the nozzle 55 or the fluid conducting tube 35 through the nozzle opening 61 when the nozzle 55 is retracted. It is therefore possible to keep the interior of the nozzle 55 and the fluid conducting tube 35 clean.

Another O-ring 76 may be used in addition to the O-ring 81 as illustrated in FIG. 13. As shown in FIG. 13, the O-ring 82 is inserted into an annular groove formed in the annular flange 25a and makes resilient contact with that portion of the distal end portion of the nozzle 55 rearward of the nozzle opening 61 when the nozzle 55 remains fully within the nozzle chamber 54. The O-ring 76 prevents dirt from entering the nozzle chamber 54 when the nozzle 55 is projected from the distal end section 25.

As shown in FIG. 14, the O-ring 81 may be inserted into an annular groove formed in that portion of the nozzle 55 which is forward of the nozzle opening 61. In this case, an O-ring 76 is disposed in the same position as shown in FIG. 13 to function as that in FIG. 13.

What is claimed is:

1. An endoscope comprising an elongated sheath having two ends, an operation section having two ends, one end being connected to one end of the sheath, a distal end section having a proximal end connected to the other end of the sheath and a distal end and a nozzle chamber formed in the distal end section, and an observation window provided on the distal end of the distal end section and having an outer surface, a cleaning device comprising:
   a hollow cylindrical nozzle reciprocatingly disposed in the nozzle chamber and having a distal end portion adapted to project from the distal end of the distal end section and recede into the distal end section according to reciprocation of the nozzle, said distal end portion having a blind end extending from the distal end of the distal end section;
   a nozzle opening formed in the distal end portion of the nozzle directed to the outer surface of the observation window when the nozzle projects from the distal end of the distal end section;
   nozzle opening and closing means provided in the distal end section for closing the nozzle opening when the nozzle recedes into the distal end section;
   a fluid passage extending through the sheath and having two ends, one end communicating with the nozzle and the other end being disposed in the operation section and connected to fluid supplying means disposed outside the operation section;
   nozzle retracting means provided in the endoscope for retracting the nozzle into the distal end section; and
   nozzle projecting means provided in the endoscope for projecting the distal end portion of the nozzle from the distal end of the distal end section when the observation window is cleaned.

2. The device according to claim 1, wherein said nozzle projecting means comprises a coil spring disposed in the distal end section and urging the nozzle toward the distal end of the distal end section.

3. The device according to claim 2, wherein said fluid passage includes a fluid conducting tube extending through the sheath and having two ends, one end communicating with the nozzle and the other end being connected to the fluid supplying means.

4. The device according to claim 3, wherein said nozzle has a proximal end portion slidably inserted in said one end of the fluid conducting tube.

5. The device according to claim 3, wherein said fluid passage includes a connecting tube extending through the distal end section and having two ends, one end being connected to said one end of the fluid conducting tube and the other end communicating with the nozzle.

6. The device according to claim 2, wherein said nozzle retracting means comprises an operating wire extending through the sheath and having two ends, one end being connected to the nozzle, and wire operating means mounted on the operation section and connected by the other end of the operating wire for pulling the operating wire together with the nozzle toward the operation section.

7. The device according to claim 1 or 2, wherein said nozzle has at least a portion made of iron, and said nozzle retracting means comprises an electromagnet disposed in the distal end section in such a position as to pull said portion of the nozzle toward the operation section and retract the nozzle into the distal end section when the electromagnet is energized.

8. The device according to claim 1, wherein said nozzle projecting means comprises a pressurized fluid introduced into the nozzle.

9. The device according to claim 8, wherein said nozzle retracting means comprises a coil spring wound around the nozzle in the distal end section and urging the nozzle toward the operation section.

10. The device according to claim 8, wherein said nozzle has at least a portion made of iron, and said nozzle retracting means comprises an electromagnet disposed in the distal end section in such a position as to pull said portion of the nozzle toward the operation section and retract the nozzle into the distal end section when the electromagnet is energized.

11. The device according to claim 1, further comprising sealing means between the distal end section and the distal end portion of the nozzle, said sealing means being positioned nearer to the distal end of the distal end section than the nozzle opening when the nozzle is retracted into the distal end section.

12. The device according to claim 11, wherein said sealing means comprises an O-ring mounted in the distal end section.

13. The device according to claim 12, wherein said sealing means further comprises an O-ring disposed in the distal end section remoter from the distal end thereof than the first-mentioned O-ring and sealingly surrounding the distal end portion of the nozzle.

14. The device according to claim 11, wherein said sealing means further comprises an O-ring mounted in a lateral wall of the distal end portion of the nozzle between the blind end and the nozzle opening.

15. The device according to claim 14, wherein said sealing means further comprises an O-ring disposed in the distal end section and sealingly surrounding the distal end portion of the nozzle.

16. The device according to claim 1, wherein said nozzle opening and closing means is a cylindrical bore portion which is formed in the distal end section and forms part of the nozzle chamber.

* * * * *